(12) United States Patent
Dolev et al.

(10) Patent No.: US 11,278,229 B2
(45) Date of Patent: Mar. 22, 2022

(54) ELECTRODE HEADSET GRID AND USE THEREOF IN THE NON-INVASIVE BRAIN STIMULATION AND MONITORING

(71) Applicant: Quantalx Neuroscience LTD, Zur Moshe (IL)

(72) Inventors: Iftach Dolev, Zur Moshe (IL); Hilla Fogel, Beit Dagan (IL)

(73) Assignee: QUANTALX NEUROSCIENCE LTD, Zur Moshe (IL)

( * ) Notice: Subject to any disclaimer, the term of this patent is extended or adjusted under 35 U.S.C. 154(b) by 985 days.

(21) Appl. No.: 15/325,819

(22) PCT Filed: Jul. 12, 2015

(86) PCT No.: PCT/IL2015/050720
§ 371 (c)(1),
(2) Date: Jan. 12, 2017

(87) PCT Pub. No.: WO2016/009424
PCT Pub. Date: Jan. 21, 2016

(65) Prior Publication Data
US 2017/0164862 A1  Jun. 15, 2017

Related U.S. Application Data

(60) Provisional application No. 62/023,885, filed on Jul. 13, 2014.

(51) Int. Cl.
*A61B 5/291* (2021.01)
*A61B 5/00* (2006.01)
(Continued)

(52) U.S. Cl.
CPC ............ *A61B 5/291* (2021.01); *A61B 5/6814* (2013.01); *A61N 1/0456* (2013.01);
(Continued)

(58) Field of Classification Search
CPC .. A61N 1/0456; A61N 1/0472; A61N 1/0476; A61N 1/0452; A61N 1/0529;
(Continued)

(56) References Cited

U.S. PATENT DOCUMENTS 4,177,817 A * 12/1979 Bevilacqua .......... A61N 1/0456
607/149
5,263,481 A   11/1993 Axelgaard et al.
(Continued)

FOREIGN PATENT DOCUMENTS

EP           1008365       2/1998
WO       2015034981       3/2015

OTHER PUBLICATIONS

Schestatsky, et al., "Simultaneous EEG Monitoring During Transcranial Direct Current Stimulation" J. Vis. Exp. (76), e50426, doi: 10.3791/50426 (2013).
(Continued)

*Primary Examiner* — Eun Hwa Kim
(74) *Attorney, Agent, or Firm* — Dorsey & Whitney, LLP (57) ABSTRACT

The present invention provides an electrode headset grid adapted to fit on a head of a human subject, the grid comprising a plurality of conductive regions, electrically isolated from each other, wherein the conductive regions are configured to contact at least one electrode, and wherein the configuration of the conductive regions is configured to define an operating electrode unit. There is further provided an integrated system for brain electric stimulation and EEG monitoring, the system comprising the electrode headset grid and a plurality of electrodes. The invention further provides use of the electrode headset grid in an integrated non-invasive brain electrical stimulation and monitoring procedure.

11 Claims, 6 Drawing Sheets

(51) Int. Cl.
*A61N 1/04* (2006.01)
*A61N 1/36* (2006.01)
*A61N 1/05* (2006.01)

(52) U.S. Cl.
CPC .. *A61N 1/36025* (2013.01); *A61B 2562/0215* (2017.08); *A61B 2562/046* (2013.01); *A61N 1/0529* (2013.01)

(58) Field of Classification Search
CPC .. A61N 1/0531; A61N 1/0541; A61N 1/0543; A61B 5/0476; A61B 5/0478; A61B 5/6803; A61B 5/6814; A61B 2562/0217
See application file for complete search history.

(56) References Cited

U.S. PATENT DOCUMENTS

| | | | |
|---|---|---|---|
| 5,833,622 | A | 11/1998 | Meathrel et al. |
| 2002/0095080 | A1 | 7/2002 | Cory et al. |
| 2006/0258788 | A1 | 11/2006 | Coggins et al. |
| 2008/0294031 | A1 | 11/2008 | Wilson et al. |
| 2009/0105576 | A1 | 4/2009 | Do et al. |
| 2009/0198305 | A1 | 8/2009 | Naroditsky et al. |
| 2011/0301683 | A1* | 12/2011 | Axelgaard ........... A61N 1/0452 607/149 |
| 2011/0319975 | A1 | 12/2011 | Ho et al. |
| 2012/0041296 | A1* | 2/2012 | Garstka .............. A61B 5/04087 600/395 |
| 2013/0281759 | A1 | 10/2013 | Hagedorn et al. |
| 2015/0065838 | A1* | 3/2015 | Wingeier ............ A61N 1/0476 600/383 |

OTHER PUBLICATIONS

Alschuler, et al., "Identifying electrode bridging from electrical distance distributions: a survey of publicly-available EEG data using a new method", Clinical Neurophysiology, 125 (2014) pp. 484-490.
International Search Report for PCT/IL2015/050720 Completed Dec. 20, 2015; dated Dec. 20, 2015 8 Pages.
Written Opinion for PCT/IL2015/050720 Completed Dec. 20, 2015; dated Dec. 20, 2015 12 Pages.

* cited by examiner

ELECTRODE HEADSET GRID AND USE THEREOF IN THE NON-INVASIVE BRAIN STIMULATION AND MONITORING

This application is a 35 U.S.C. § 371 national phase application of PCT/IL2015/050720, filed Jul. 12, 2015, which claims priority to U.S. 62/023,885 filed on Jul. 13, 2014. Both applications are incorporated herein by reference as if fully set forth.

FIELD OF THE INVENTION

Embodiments of the disclosure relate to an electrode headset grid comprising a plurality of conductive regions, electrically isolated from each other, a system including the electrode headset grid and a plurality of electrodes and use of said grid in the integrated non-invasive brain stimulation and monitoring procedure.

BACKGROUND

The recent emergence of noninvasive brain stimulation techniques for inducing reversible changes in brain activity has allowed not only studying mechanisms underlying perceptual, motor, and cognitive functions, but also provided the ability to modulate these functions in the human brain. The non-invasive stimulation techniques used to modulate cortical activity include transcranial magnetic stimulation (TMS) and transcranial electrical stimulation (tES). The tES technique involves the application of weak electrical currents directly to the head of a subject for several minutes. These currents generate an electrical field that modulates neuronal activity according to the duration, intensity, and modality of the application, which can be direct (transcranial direct current stimulation (tDCS)), alternating (transcranial alternating current stimulation (tACS)), or random noise (transcranial random noise stimulation (tRNS)).

Transcranial direct current stimulation (tDCS) is a non-invasive, painless brain stimulation treatment that uses direct electrical currents to stimulate specific parts of the brain. A constant, low intensity current is passed through two electrodes placed over the head which modulates neuronal activity. There are two types of stimulation with tDCS: anodal and cathodal stimulation. Anodal stimulation acts to excite neuronal activity while cathodal stimulation inhibits or reduces neuronal activity.

Transcranial direct current stimulation is actively investigated to treat a wide range of neuropsychiatric disorders, such as depression, anxiety, Parkinson's disease, and chronic pain, to facilitate stroke rehabilitation, and as a research tool to modify cognitive processes. The most common side effect of tDCS is a slight itching or tingling on the scalp.

The degree of sensation during tDCS is associated with electrode design, and is important for both tolerability, influence on cognitive tasks, and sham reliability. Typically, some form of sponge, saturated in saline or water (tap or distilled), is placed on the skin. The electrode may be either placed on the distal surface of the sponge (e.g. a metal grid), be inside a sponge 'pocket' (e.g. rubber electrodes), or even be alligator clips attached to a sponge edge. Use of gel to improve conductance or wetting of electrodes with conductive solution prior to stimulation procedure is also common during tDCS.

The combination of non-invasive stimulation with neuroimaging techniques has gained popularity in recent years, due to its potential to examine the state of targeted brain areas and the roles of these areas in specific functions. tES can be combined with functional magnetic resonance (fMRI), positron emission tomography (PET) or electroencephalography (EEG), to provide several advantages including the opportunity to collect objective and direct measurements of brain activity. A significant advantage of functional neuroimaging is the ability to acquire simultaneous measurements of activity in the entire brain, thereby providing a broader picture of the cortical responses to any given condition.

US Patent Application No. 2013/0281759 is directed to a technology providing combination electroencephalography and non-invasive stimulation devices. Upon measuring an electrical anomaly in a region of a brain, various non-invasive stimulation techniques are utilized to correct neural activity, including transcranial direct current stimulation, transcranial alternating current stimulation and transcranial random noise stimulation, low threshold transcranial magnetic stimulation and repetitive transcranial magnet stimulation.

The clear utility of tES-EEG lies in the fact that the observed signals are directly coupled to neuronal electrical activity. That is, the EEG recordings reflect the electric potential resulting from synaptic transmembrane currents in neurons that are (or are not) modified by tES. Moreover, this approach offers the potential to identify responses to tES within an area or across circuits, thereby helping to determine in vivo the brain areas that are directly or indirectly affected by tES.

Conventional EEG wet-electrode sensor assemblies include an Ag/AgCl disc (or a disc of some other conductive material). A wet conductive gel is used to establish an electrical connection through any hair between the subject area and the Ag/AgCl disc. Electrical potentials on the surface of the subject area are coupled through the gel to the Ag/AgCl disc and into an electronic amplifier. A standard wet electrode sensor assembly provides a secure, low-impedance electrical connection between the subject area and a recording instrument, and thereby ensures high quality signal sensing. However, the use of electrolytic gels in combination with the need for skin preparation is often time consuming for the user to set up, skin-irritating and inconvenient for the subject. Alternatively, dry electrodes, which are designed to push through the hair to directly contact the scalp and do not require conductive gels or scalp preparation, have been explored as alternatives to wet electrodes. Typically, dry EEG electrodes utilize straight, hard fingers that are designed to push through strands of hair to the scalp.

US Patent Application No. 2009/0105576 is directed to an apparatus and technique for sensing biopotential signals wherein a conductive element is formed from a non-adhesive hydrogel material and configured to provide a conductive path between an electrode and a subject's skin for transmitting EEG signals from the subject to the electrode.

Integrated tES-EEG techniques can be divided into two methodological approaches: the offline method, which evaluates the short- and long-term aftereffects induced by brain stimulation, and the interactive approach, which evaluates the immediate changes that occur during the stimulation. In the interactive approach, EEG is used to probe the state of the cortical area affected by tES, which could be the target area of the stimulation or an interconnected region, and to evaluate the changes in excitability and connectivity within a functional network.

The offline method requires changing of electrodes between the stimulation and EEG measurement, which complicates the overall procedure. Further, application of EEG electrodes following stimulation requires thorough wiping of the skull, making the combined tDCS-EEG procedure even more time-consuming.

Typically, for the interactive approach, stimulation electrodes and EEG electrodes are positioned at the predetermined sites on the subject's head, such that EEG is not measured directly at the area to which stimulation is applied. Additionally, function of an electrode (stimulation or EEG) or its position on the subject's head cannot be altered during the procedure.

The positioning and number of the stimulation and EEG electrodes are confined by several factors. While dry electrodes can be used for EEG, tDCS still requires application of a conductive fluid or gel to the subject's head at the electrode contact site. In the interactive tDCS-EEG procedure use of such fluid or gel limits a number of EEG electrodes that can be applied to a subject's head concurrently with the stimulation electrodes. EEG electrodes exposed to the same conductive aqueous media will bridge and function as one electrode, severely distorting or spatially smoothing an EEG topography, confounding conventional descriptions and inferences while invalidating source localization estimates [D. M. Alschuler et al. Clinical Neurophysiology 125 (2014) 484-490]. Thus, EEG electrodes should be positioned within a sufficient distance from each other in the presence of conductive gel or saline to prevent the low impedance bridging of the electrodes. Additionally, when using conventional sponge electrodes for tDCS-EEG, the total number of electrodes is limited by the stimulation electrode size, which is generally in the range of 25-35 cm$^2$. Thus, use of multiple electrodes for combined stimulation and EGG is hindered by the application of electrolyte, as well as by the size of the stimulation electrodes, limiting the spatial resolution, effectiveness and flexibility of the integrated tES-EGG process.

Use of a same electrode for both electric stimulation and EEG is generally impossible, due to the different requirements of said electrodes and procedures. The only presently available commercial combined electrode, which can be used for both tCS and EEG, is a PISTIM Pi cm$^2$ Electrode of Neuroelectrics, Barcelona, Spain with 3.14 cm$^2$ area and Ag/AgCl gel-based stimulation electrode with rear-fill aperture for gel supply. This Ag/AgCl electrode can be used for both stimulation and EEG. However, this electrode must be used with a conductive gel [http://www.neuroelectrics.com/sites/neuroelectrics.com/files/enobio/Electrodes_User_Manual.pdf]. In a conventional integrated tES-EEG procedure said electrodes are operated by StarstimÖ—Neuroelectrics Instrument Controller, having eight channels, such that each electrode can be used for the EEG (six channels) and for tDCS (two channels for sponge-electrodes, the anode and the cathode). In some circumstances, more than two sites of stimulation can be used. In this case four sponge-electrodes will be required and consequently, only 4 channels will remain for EEG recordings [Schestatsky, P., Morales-Quezada, L., Fregni, F. Simultaneous EEG Monitoring During Transcranial Direct Current Stimulation. J. Vis. Exp. (76), e50426, doi:10.3791/50426 (2013)].

There, thus, remains an unmet need for an integrated tES and EEG device, which would allow using the same electrode for both electrical stimulation and EEG. Such device would facilitate concurrent use of multiple electrodes for both EEG monitoring and electrical stimulation, thus providing a highly modular, accurate and efficient integrated tES-EEG procedure.

SUMMARY

The following embodiments and aspects thereof are described and illustrated in conjunction with systems, tools and methods which are meant to be exemplary and illustrative, not limiting in scope.

The present invention is directed to an electrode headset grid, which allows carrying out simultaneous transcranial electric stimulation and electroencephalographic recording, wherein each electrode connected to said grid can function both as a stimulation or as a recording electrode. The electrode headset grid of the present invention can beneficially be used in combination with any conventional electrode array in the integrated tES-EEG procedure. This advantageous feature of the electrode headset grid is attributed to the specific properties of the grid, including the configuration, structure and/or composition of the conductive regions thereof, which are configured to accommodate an array of conventional electrodes. The electrode headset grid can be further combined with an operating system, wherein said system is configured to define stimulation and recording parameters of the electrodes contacting said conductive regions.

Thus, in one aspect there is provided an electrode headset grid adapted to fit on the head of a human subject, the grid comprising a plurality of conductive regions, electrically isolated from each other, wherein said conductive regions are configured to contact at least one electrode, and wherein the configuration of said conductive regions is configured to define an operating electrode unit. The electrode headset grid of the present invention can be used in combination with a non-disposable electrode array. According to some embodiments, the operating electrode unit comprises a defined number of electrodes being in ionic contact with each other. According to other embodiments, the operating electrode unit comprises a defined number of electrodes functioning as one electrode.

In some embodiments, the electrode headset grid comprises 1-1000 conductive regions. In some embodiments, the configuration of said conductive regions comprises number of said conductive regions. In other embodiments, the configuration of said conductive regions comprises size of said conductive regions. In additional embodiments, the configuration of said conductive regions comprises position of said conductive regions relatively to the electrode headset grid.

According to some embodiments, the conductive regions comprise channels. According to further embodiments, said channels are hollow. According to still further embodiments, the channels are filled with a conductive material. In some embodiments, said conductive material is solid. In other embodiments, said conductive material is a non-leaking material. In further embodiments, said conductive material comprises a super absorbent polymer (SAP). In still further embodiments, said SAP comprises a hydrogel. In certain embodiments, said SAP comprises a polyacrylate salt.

In some embodiments, the conductive regions further comprise metal insertions. In other embodiments, the channels further comprise metal insertions.

According to further embodiments, the electrode headset grid is formed of a non-conducting material. According to still further embodiments, said grid is flexible. According to yet further embodiments, said grid is disposable. According to still further embodiments, said grid is sterile.

According to some embodiments, each of said plurality of conductive regions is configured to accommodate at least one electrode. According to further embodiments, each of said plurality of conductive regions is configured to accommodate 1-1000 electrodes. According to still further embodiments, the plurality of conductive regions are configured to accommodate 1-1000 electrodes In another aspect, the invention provides an integrated system for brain electric stimulation and EEG monitoring, the system comprising:

a. a plurality of electrodes having conducting means to carry electrical signals to and from the plurality of electrodes; and b. an electrode headset grid adapted to fit on the head of a human subject, the grid comprising a plurality of conductive regions, electrically isolated from each other, wherein said conductive regions are configured to contact at least one of said electrodes, and wherein the configuration of said conductive regions is configured to define an operating electrode unit.

According to some embodiments, said plurality of electrodes is in electric contact with said plurality of conductive regions. According to further embodiments, the number of conductive regions is equal to the number of electrodes. According to other embodiments, the number of conductive regions is smaller than the number of electrodes. According to additional embodiments, each of said plurality of conductive regions comprises 1-1000 electrodes.

According to further embodiments, each electrode of said plurality of electrodes is configured to function as an EEG monitoring electrode, as a stimulating electrode or a combination thereof. Each possibility represents a separate embodiment of the invention. According to still further embodiments, each electrode of said plurality of electrodes is configured to function as an anode, a cathode or a combination thereof. Each possibility represents a separate embodiment of the invention. According to yet further embodiments, each electrode of said plurality of electrodes is configured to function as a working electrode, a reference electrode, a non-functioning electrode or a combination thereof. Each possibility represents a separate embodiment of the invention. According to still further embodiments, each electrode of said plurality of electrodes is configured to function as a working electrode, a reference electrode, a non-functioning electrode or a combination thereof, when contacting at least one conductive region. Each possibility represents a separate embodiment of the invention.

According to additional embodiments, each of said operating electrode units is configured to function as an EEG monitoring electrode, as a stimulating electrode or a combination thereof. Each possibility represents a separate embodiment of the invention. According to further embodiments, each of said operating electrode units is configured to function as an anode, a cathode or a combination thereof. Each possibility represents a separate embodiment of the invention. According to still further embodiments, each of said operating electrode units is configured to function as a working electrode, a reference electrode, a non-functioning electrode or any combination thereof. Each possibility represents a separate embodiment of the invention.

In some embodiments, said plurality of electrodes comprises silver electrodes, silver—silver chloride electrodes or gold electrodes. Each possibility represents a separate embodiment of the invention.

In some embodiments, a contact between the plurality of electrodes and the subject's head is accomplished through the conductive regions of the electrode headset grid. In other embodiments, the electrode headset grid is configured to physically isolate said plurality of electrodes from the subject's head.

In further embodiments, the integrated system comprises an operating system. In some embodiments, the operating system is configured to induce EEG monitoring via the plurality of electrodes. In other embodiments, the operating system is configured to induce electrical stimulation via the plurality of electrodes. In the preferred embodiments, the operating system is configured to induce EEG monitoring and electrical stimulation via the same plurality of electrodes. In further embodiments, the operating system is configured to define EEG monitoring and/or electrical stimulation parameters.

In yet another aspect, there is provided a method of carrying out an integrated non-invasive brain electrical stimulation and monitoring procedure, comprising the steps of: placing on a head of a human subject an electrode headset grid comprising a plurality of conductive regions, electrically isolated from each other, wherein said conductive regions are configured to contact at least one electrode, and wherein the configuration of said conductive regions is configured to define an operating electrode unit; contacting the electrode headset grid with a plurality of electrodes; inducing a non-invasive electrical stimulation of the brain of said human subject via the plurality of electrodes; and inducing EEG measurement of electrical currents within a brain of said human subject via a plurality of electrodes, thereby obtaining EEG signals.

In some embodiments, the steps of inducing EEG measurement and/or inducing electrical stimulation are performed repeatedly. In the preferred embodiments, the EEG measurement and the electrical stimulation are performed via the same plurality of electrodes.

In the integrated non-invasive brain electrical stimulation and monitoring procedure of the present invention, the EEG measurement and/or the electrical stimulation can be performed according to an algorithm. In some embodiments, the algorithm is configured to define EEG measurement and/or electrical stimulation parameters. In some embodiments, the EEG measurement and/or electrical stimulation parameters comprise polarity of the electrodes, comprising an anode, a cathode or a combination thereof. Each possibility represents a separate embodiment of the invention. In other embodiments, the EEG measurement and/or electrical stimulation parameters comprise stimulation regimen, comprising transcranial direct current stimulation (tDCS), transcranial alternating current stimulation (tACS), transcranial random noise stimulation (tRNS) or combinations thereof. Each possibility represents a separate embodiment of the invention. In additional embodiments, the EEG measurement and/or electrical stimulation parameters comprise the electrodes mode of functioning, comprising a working electrode, a reference electrode, a non-functioning electrode or any combination thereof. Each possibility represents a separate embodiment of the invention. In further embodiments, the EEG measurement and/or electrical stimulation parameters comprise the position of electrodes used for EEG measurement and/or electrical stimulation relative to the head of a human subject.

The algorithm may be further configured to alter the EEG measurement and/or electrical stimulation parameters during the integrated non-invasive brain electrical stimulation and monitoring procedure. The method of the present invention may further include a step of interchanging the electrode headset grid with an electrode headset grid having a different configuration of said conductive regions, during the integrated non-invasive brain electrical stimulation and monitoring procedure. In such embodiments, the operating units' configuration, and the EEG measurement and electrical stimulation parameters can be changed in order to provide flexibility to the integrated non-invasive brain electrical stimulation and monitoring procedure In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. It is intended that the embodiments and figures disclosed herein are to be considered illustrative rather than restrictive. The figures are listed below.

DETAILED DESCRIPTION

The present invention relates to an electrode headset grid and to a non-invasive system which combines transcranial stimulation with high spatial resolution EEG. Said system is configured to enable full flexibility of electrode configuration montage and function and/or robust operation option for changing configuration and function while operating. According to some embodiments, the system is configured to be operated by a custom algorithm. The integrated system, according to some embodiments of the invention, comprises a plurality of electrodes and an electrode headset grid, comprising conductive regions.

Without wishing to be bound by any specific mechanism or theory of action, each electrode of the plurality of electrodes can be used for either EEG monitoring or stimulation at any given time, allowing on-line flexibility for determining and altering stimulation conditions, including number of electrodes, radius of stimulation, electrode location or polarity of stimulation. Each electrode can also be used as an EEG working electrode or reference electrode before, during or following stimulation. The electrode can also be a non-functioning electrode. The electrode mode of functioning (working, reference, non-functioning) can be altered during the EEG and/or stimulation procedure. Electrode flexibility between EEG recording and stimulation is also configured to enable changing stimulation parameters before, during and/or after stimulation, wherein stimulation properties include, inter alia, polarity or type of current. Said flexibility of electrode parameters is particularly advantageous for use in complex protocols of treatment, determined by algorithm for personalized and individualized treatment. Without further wishing to being bound by a specific mechanism of action, while the physical placement of the plurality of electrodes is predetermined and not flexible, the flexibility in all levels of freedom described hereinabove is achieved by the electrode headset grid, which is configured to provide a non-invasive high spatial resolution EEG recordings as well as electric stimulation. The electrode headset grid, according to some embodiments of the invention, can advantageously be used without application of any wet agent, such as, for example, conductive gel, lubricant or saline solution. According to further embodiments, the electrode headset grid provides continuous interface between the plurality of electrodes and the head of a subject, thus enabling high resolution EEG recordings as well as electrical stimulation for non-invasive brain stimulation. Without further wishing to being bound by a specific mechanism of action, using the electrode headset grid, according to some embodiments of the invention, enables a combination of EEG and electrical stimulation from a large amount of electrodes, while preventing the electrodes bridging through the mutual wet agent. In the preferred embodiments, the number, configuration and position of the plurality of electrodes is defined not by the electrodes' properties, but by the configuration of the electrode headset grid used. According to some embodiments, the grid configuration is configured to define the maximal number of configurations, protocols and montages available using a specific electrode headset grid. Use of said electrode headset grid, according to embodiments of the invention, for EEG recordings further allows minimizing noise and increasing signal-to-noise ratio (SNR). Use of said electrode headset grid, according to embodiments of the invention, for electrical stimulation further provides alleviation of side effects such as, for example, irritation of the skin. In the preferred embodiments of the invention the conductive regions of the electrode headset grid comprise a non-leaking conductive material, wherein said regions are electrically isolated from each other, and wherein said non-leaking conductive material is configured to provide continuous conductive interface between electrodes and subject's skin.

Thus, according to a first aspect, the invention provides an electrode headset grid adapted to fit on the head of a human subject, the grid comprising a plurality of conductive regions, electrically isolated from each other, wherein said conductive regions are configured to contact at least one electrode, and wherein the configuration of said conductive regions is configured to define an operating electrode unit. The term "operating electrode unit" as used herein, refers in some embodiments to a defined number of electrodes being in ionic contact with each other. In other embodiments, the term "operating electrode unit" refers to a defined number of electrodes functioning as one electrode. In further embodiments, the number of said electrodes is defined by the configuration of said conductive regions. The term "configuration of conductive regions", as used herein, relates in some embodiments to the number of the conductive regions, position of the conductive regions, size of the conductive regions or any combination thereof relatively to the electrode headset grid.

In some embodiments of the invention, said conductive regions configuration is configured to define radius of stimulation and/or spatial resolution of EEG monitoring. In further embodiments, said conductive regions configuration is configured to define a number or operating electrodes and/or position thereof relative to the electrode headset grid. In additional embodiments, said conductive regions configuration is configured to define a number or operating electrodes and/or position thereof relative to the subject's head.

The electrode headset grid may comprise 1-1000 conductive regions, such as for example, 1-4 conductive regions, 6-8 conductive regions, 9-12 conductive regions, 16-24 conductive regions, 25-48 conductive regions, 49-100 conductive regions, 120-240 conductive regions, 250-480 conductive regions or 500-1000 conductive regions. Alternatively, the electrode headset grid may comprise 1-1000 operating electrode units, such as for example, 1-4 operating electrode units. 6-8 operating electrode units, 9-12 operating electrode units, 16-24 operating electrode units, 25-48 operating electrode units, 49-100 operating electrode units, 120-240 operating electrode units, 250-480 operating electrode units or 500-1000 operating electrode units.

According to further embodiments, the electrode headset grid comprises 1-1000 conductive regions, such as for example, 1, 2, 4, 6, 8, 12, 24, 48, 100, 250, 500 or 1000 conductive regions. The electrode headset grid may further comprise 1-1000 operating electrode units, such as for example, 1, 2, 4, 6, 8, 12, 24, 48, 100, 250, 500 or 1000 operating electrode units.

In some embodiments, the electrode headset grid comprises at least 2 conductive regions. In further embodiments, the electrode headset grid comprises at least 4 conductive regions, preferably at least 6, more preferably at least 9, more preferably at least 12, more preferably at least 20, more preferably at least 36, more preferably at least 48 conductive regions. In some embodiments, the electrode headset grid comprises at least 2 operating electrode units. In further embodiments, the electrode headset grid comprises at least 4 operating electrode units, preferably at least 6, more preferably at least 9, more preferably at least 12, more preferably at least 20, more preferably at least 36, more preferably at least 48 operating electrode units.

In some exemplary embodiments, the electrode headset grid comprises 2 conductive regions. In further exemplary embodiments, the electrode headset grid comprises 12 conductive regions. In additional exemplary embodiments, the electrode headset grid comprises 48 conductive regions. In some exemplary embodiments, the electrode headset grid comprises 2 operating electrode units. In further exemplary embodiments, the electrode headset grid comprises 12 operating electrode units. In additional exemplary embodiments, the electrode headset grid comprises 48 operating electrode units.

In some embodiments, the conductive regions are homogeneously distributed along the electrode headset grid. In further embodiments, the conductive regions are distributed to provide symmetrical coverage of the right and left brain regions. According to other embodiment, the conductive regions are non-homogeneously distributed along the electrode headset grid. In further embodiments, the conductive regions position is determined by a personalized treatment protocol of a subject.

The conductive regions of the electrode conductive grid may have any shape, such as, for example, cylinder, spherical or rectangular. The shape of the plurality of the conductive regions may be same or different. Additionally, the size of the plurality of the conductive regions may be same or different. In the preferred embodiments, the plurality of conductive regions comprises uniform shape and size.

In some embodiments, the conductive region has an area in the range of about 0.03 cm$^2$ to about 4000 cm$^2$, such as, for example, in the range of about 0.05 cm$^2$ to about 1000 cm$^2$, in the range of about 0.1 cm$^2$ to about 500 cm$^2$, in the range of about 0.5 cm$^2$ to about 100 cm$^2$, or in the range of about 1 cm$^2$ to about 10 cm$^2$. Each possibility represents a separate embodiment of the invention.

As used herein, the term "about", when referring to a measurable value such as an amount, a temporal duration, and the like, is meant to encompass variations of +/−10%, more preferably +/−5%, even more preferably +/−1%, and still more preferably +/−0.1% from the specified value, as such variations are appropriate to perform the disclosed methods.

In some embodiments, the conductive region has a cylinder shape. The radius of said cylinder shaped conductive region may be in the range from about 1 mm to about 30 cm. In further embodiments, the radius of the cylinder shaped conductive regions is in the range of about 5 mm to about 10 cm or of about 10 mm to about 50 mm. Each possibility represents a separate embodiment of the invention.

The conductive regions of the electrode headset grid may comprise channels formed within said grid. In the preferred embodiments, said channels are cylinder. Said channels may have at least one open end. In other embodiments, said channels have two open ends. In additional embodiments said channels are hollow.

In further embodiments, said channels are filled with a conductive material. In additional embodiments, the conductive material fills at least 50% of the channels volume, such as, for example, 60%, 70%, 80%, 90% or 100% of the channels volume. Each possibility represents a separate embodiment of the invention.

The conductive material may be solid or a semi-solid. Each possibility represents a separate embodiment of the invention. In particular embodiments, the conductive material is solid. In further embodiments, the conductive material is a non-leaking material.

In further embodiments, the conductive material comprises a super absorbent polymer (SAP). The term "super absorbent polymer" as used herein refers to a polymer which is capable, in its dry state, to spontaneously absorb at least 20 times its own weight of aqueous fluid, in particular of water and especially of distilled water. The super absorbent polymer may comprise a hydrogel. In some embodiments the hydrogel is cross-linked. The non-limiting examples of SAP suitable for use in the headset grid of the present invention include polyacrylate, such as, but not limited to diethylaminopropyl acrylates and methacrylates, including sodium, potassium, lithium or ammonium salts thereof; polyacrylamide; polysaccharides, such as carboxymethyl starch, carboxymethyl cellulose, or hydroxypropyl cellulose; polyvinyl alcohol or polyvinyl ethers; polyvinyl pyridine, or cross-linked polyethylene oxide. In the preferred embodiments, the SAP is a polyacrylate salt. Super absorbent polymers can be made using one of three primary methods; gel, polymerization, suspension polymerization or solution polymerization.

The SAP may be filled with a conductive solution, such as, but not limited to, NaCl solution, KCl solution, CaCl$_2$ solution or MgCl$_2$ solution. Each possibility represents a separate embodiment of the invention. The SAP may be filled with the conductive solution prior to performing the integrated EEG measurement and electrical stimulation procedure. In other embodiments, the SAP is filled with the conductive solution upon manufacture of the electrode headset grid. In the preferred embodiments, the electrode headset grid does not require use of any additional conductive fluid or gel for electrical stimulation and/or integrated EEG monitoring and stimulation. The conductivity of the SAP filled with the conductive solution may be in a range of about 5-100 mS/cm at 25° C.

The channels of the electrode headset grid may further include metal insertions. Said metal insertions are configured to improve electric contact between the electrode and the super absorbent polymer. In other embodiments, the metal insertions are configured to improve electric contact between the electrode and the subject's head. The metal insertions may be in a form of a net, positioned within the channel. In some embodiments, said net contacts inner walls of the channel. In other embodiments, said net covers at least one open end of the channel.

The metal insertion may be formed of any metal compatible with the conductive solution of the super absorbent polymer. The non-limiting examples of the metals include: silver, platinum, gold, copper, aluminum, nickel. The metal insertion may further be coated with a corresponding salt of said metal, wherein said salt has a low solubility in water. The non-limiting example of suitable salt includes AgCl In some embodiments of the invention, the electrode headset grid is formed from a non-conducting material, such as, but not limited to, rubber or silicon. In other embodiments the electrode headset grid is flexible. In further embodiments, the electrode headset grid is configured to fit on a subject's head. In some embodiments, the size of the electrode headset grid is fixed. Alternatively, the electrode headset grid may be manufactured in different sizes, matching subject's head sizes. The electrode headset grid may further comprise means for adjusting said grid to the head of the human subject, including, but not limited to straps.

The electrode headset grid may be a multiple use or a single use grid. In the preferred embodiments, the electrode headset grid is disposable. In other embodiments, the electrode headset grid is sterile. The grid may be packed and saved sterile until open for use. The sterility and disposability of the grid are specifically important, as the grid is configured to contact patient's head. In some embodiments, the grid is configured to contact patient's head such that the electrodes do not come in direct contact with the head. Thus, the electrode headset grid is configured to provide an intermediate layer between the head of the subject and the electrodes. Without wishing to being bound by any specific theory or mechanism of action, since the conductive grid is sterile and disposable it ensures an optimal, constant, repeatable and reliable quality of used electrodes in terms of electrical properties such as impedance and minimal irritation to the treated skin.

The electrode headset grid of the present invention is configured to be used in combination with an electrode array. The electrode array may comprise a plurality of electrodes. Said electrode array may be a multi-use electrode array and/or a non-disposable electrode array. In further embodiments, the electrode array comprises a non-variable number of electrodes. The electrode array may further comprise an isolating base, incorporating the electrodes. The electrode array may comprise any electrodes, suitable for use in EEG recording and/or electrical stimulation, such as, but not limited to platinum (Pt) electrodes, silver electrodes or silver-silver chloride (Ag/AgCl) electrodes.

In some embodiments of the invention, the electrode array comprises 20-1000 electrodes for partial to full scalp capture, such as, for example, 20, 256, 350, 512 or 750 electrodes. Each possibility represents a separate embodiment of the invention.

According to further embodiments, the electrode array comprises electrodes having a radius in the range of about 1 mm to about 3 cm.

In further embodiments, each of the plurality of the conductive regions of the electrode conductive grid is configured to accommodate at least one electrode of said electrode array. In further embodiments, each of the channels is configured to accommodate at least one electrode.

In some embodiments, each of the plurality of conductive regions is configured to accommodate 1-1000 electrodes. In further embodiments, each of the plurality of conductive regions is configured to accommodate up to about 20 electrodes, up to about 25 electrodes, up to about 50 electrodes, up to about 80 electrodes or up to about 110 electrodes. In yet further embodiments, the plurality of the conductive regions is configured to accommodate 1-1000 electrodes, such as, for example, 50-500 electrodes or 100-250 electrodes. In some embodiments, each of the plurality of conductive regions is configured to accommodate at least 1 electrodes, at least 2 electrodes, at least 5 electrodes, at least 10 electrodes, at least 20 electrodes, at least 50 electrodes or at least 100 electrodes. Each possibility represents a separate embodiment of the invention.

According to further embodiments, there is provided an electrode headset grid, adapted to fit on the head of a human subject, the grid comprising a plurality of conductive regions, electrically isolated from each other, wherein said conductive regions are configured to contact at least one electrode, and wherein the configuration of said conductive regions is configured to define an operating electrode unit; and further comprising a plurality of electrodes, wherein said electrodes are in electric contact with said conductive regions. In some embodiments of the invention, the electric contact between the plurality of electrodes and the subject's head is accomplished through the plurality of the conductive regions.

In some embodiments, the number of conductive regions is equal to the number of electrodes. In other embodiments, the number of conductive regions is smaller than the number of electrodes.

In further embodiments of the invention, each of the plurality of electrodes is configured to function as an EEG monitoring electrode, as a stimulation electrode or a combination thereof. In yet further embodiments, each of the plurality of electrodes is configured to function as an anode, as a cathode or a combination thereof. In still further embodiments, each of the plurality of electrodes is configured to function as a working electrode, as a reference electrode, a non-functioning electrode or any combination thereof.

In further embodiments of the invention, each of the operating electrode units, comprising a defined number of electrodes being in ionic contact with each other, is configured to function as an EEG monitoring electrode, as a stimulation electrode or a combination thereof. In yet further embodiments, each of the operating electrode units is configured to function as an anode, as a cathode or a combination thereof. In still further embodiments, each of the operating electrode units is configured to function as a working electrode, as a reference electrode, as a non-functioning electrode or any combination thereof.

In another aspect there is provided an integrated system for brain electric stimulation and EEG monitoring, the system comprising a plurality of electrodes having conducting means to carry electrical signals to and from the plurality of electrodes; and an electrode headset grid adapted to fit on the head of a human subject, the grid comprising a plurality of conductive regions, electrically isolated from each other, wherein said conductive regions are configured to contact at least one of said electrodes, and wherein the configuration of said conductive regions is configured to define an operating electrode unit. According to some embodiments, the plurality of electrodes comprises a fixed number of electrodes and/or fixed configuration array. According to some embodiments, the use of the integrated system comprising a combination of the electrode headset grid of the present invention in combination with a fixed electrodes configuration array provides a highly flexible brain monitoring and stimulating system with high accuracy, definition, and reliability.

In some embodiments, each conductive region comprises 1-1000 electrodes. In further embodiments, each conductive region comprises at least 1 electrodes, at least 5 electrodes, at least 10 electrodes, at least 20 electrodes, at least 50 electrodes or at least 100 electrodes.

According to some embodiments, the electrode headset grid is configured to be interchanged with another electrode headset grid, having different configuration of conductive regions, during the brain electric stimulation and/or EEG monitoring. In some embodiments the electrode headset grid is configured to contact the head of a human subject. In other embodiments, the electrodes do not directly contact the head of a human subject.

According to further embodiments, the integrated system further comprises an operating system, configured to induce EEG monitoring via the plurality of electrodes. According to yet further embodiments, the integrated system further comprises an operating system, configured to process, store, display and/or analyze EEG signals from the plurality of electrodes. According to still further embodiments, the operating system is configured to induce the electrical stimulation via the plurality of electrodes. According to still further embodiments, the operating system is configured to induce the electrical stimulation and EEG monitoring via the same plurality of electrodes. In further embodiments, each electrode in the electrode array can be used for both electrical stimulation and EEG monitoring. In yet further embodiments, each operating electrode unit can be used for both electrical stimulation and EEG monitoring.

According to still further embodiments, the operating system is configured to induce EEG monitoring and/or electrical stimulation according to an algorithm. According to yet further embodiments, the operating system is configured to induce EEG monitoring and/or electrical stimulation according to a predefined algorithm. According to still further embodiments, said algorithm is adapted for a personalized treatment of said subject.

In additional embodiments, the operating system is configured to define EEG monitoring and/or electrical stimulation parameters. In further embodiments, the operating system is configured to define EEG monitoring and/or electrical stimulation parameters according to a predefined algorithm. Said EEG monitoring and/or electrical stimulation parameters include, but are not limited to, polarity of the electrodes, including an anode, a cathode or a combination thereof; stimulation current type, including DC, AC or a combination thereof; stimulation regimen, including tDCS, tACS, tRNS or any combination thereof; stimulation current amplitude; stimulation current waveform; stimulation current pulse length and width; frequency, electrode mode of functioning, including working, reference, non-functioning or a combination thereof; or position of electrode used for stimulation and/or EEG monitoring.

In further embodiments, the electrode mode of functioning is determined by the configuration of the conductive regions of the electrode headset grid, by the operating system or by a combination thereof. Without wishing to being bound by any specific mechanism of action, while the configuration of the conductive regions is configured to determine whether an electrode will be an operating electrode (i.e. being in contact with the conductive region of the electrode headset grid) or a non-operating electrode (i.e. not being in contact with the conductive region of the electrode headset grid), the operating system is further configured to define the mode of functioning of the operating electrode, including EEG or stimulation; anode or cathode; working, reference or non-functioning.

In some embodiments, said predefined algorithm depends on the configuration of the conductive regions of the electrode headset grid used. In other embodiments, said algorithm is configured to define the configuration of the conductive regions of the electrode headset grid to be used. In further embodiments, said algorithm is configured to induce interchanging of the electrode headset grids having different conductive regions configuration.

In further embodiments, said algorithm is a self-learning algorithm. Said algorithm can further be configured to alter EEG monitoring and/or electrical stimulation parameters in response to the obtained EEG signals in real time.

In further embodiments, the algorithm is configured to induce EEG monitoring and/or electrical stimulation relatively to a defined skull region. In further embodiments, the algorithm is configured to allow application of a combined protocol in different areas on the skull for different stimulation properties in different brain areas can be applied For example, while one brain region can receive a tDCS anodal stimulation protocol for a defined period of time, another brain region can receive a tACS or tRNS stimulation protocol for a different period of time, while other electrodes at the same time operate as EEG recording electrodes or reference electrodes.

According to further embodiments, the operating system is configured to continuously check impedance of the operating electrodes. The operating system is further configured to provide indication of the electrode having increased impedance. In further embodiments, the integrated system for EEG monitoring and electrical stimulation allows replacement of the closest electrode to the one, having increased impedance, to ensure ongoing recording and treatment with minimal abruptions.

In some embodiments, the algorithm is user operated. In other embodiments, the algorithm is configured to provide an independent closed loop system stimulating and EEG monitoring, while changing stimulation settings and electrode montages by changing conductive region configuration of the electrode headset grid, for personalized best fitted treatment.

In some embodiments, the integrated system of the present invention is configured to provide a high spatial resolution EEG measurement. According to further embodiments, the integrated system provides signal-to-noise ratio increase. According to further embodiments, the integrated system for brain electrical stimulation an EEG monitoring provides alleviation or elimination of skin irritation side effect of the electric stimulation procedure.

In further embodiments, said integrated system includes means to electronically connect to the operating system. Said means may include wires, co-axial cable or a combination thereof. In some embodiments, the electrodes are connected to the operating system through wires and co-axial cable. In other embodiments, the electrodes are connected to the operating system through a pre-amplifier. In further embodiments, the electrodes are connected to the operating system through wires, co-axial cable a pre-amplifier.

In another aspect there is provided a method of carrying out integrated non-invasive brain electrical stimulation and monitoring, comprising the steps of:

placing an electrode headset grid adapted to fit on the head of a human subject, the grid comprising a plurality of conductive regions, electrically isolated from each other, wherein said conductive regions are configured to contact at least one electrode, and wherein the configuration of said conductive regions is configured to define an operating electrode unit, on the head of a human subject;

contacting the conductive regions of said electrode headset grid with a plurality of electrodes;

inducing a non-invasive electrical stimulation of the brain of said human subject via the plurality of electrodes; and inducing EEG measurement of electrical currents within a brain of said human subject via the plurality of electrodes, thereby obtaining EEG signals.

The step of inducing a non-invasive electrical stimulation may comprise sending an electric current to the brain of the human subject via the plurality of electrodes. According to some embodiments, the step of inducing EEG measurement can be performed repeatedly. According to some embodiments, the step of inducing electrical stimulation can be performed repeatedly. According to some embodiments, the step of inducing EEG measurement is performed prior to the step of electrical stimulation. According to other embodiments, the step of inducing EEG measurement is performed following the step of electrical stimulation. According to other embodiments, the step of inducing EEG measurement is performed both prior to and following the step of electrical stimulation.

In some embodiments of the invention, the method includes:

a. placing an electrode headset grid adapted to fit on the head of a human subject, the grid comprising a plurality of conductive regions, electrically isolated from each other, wherein said conductive regions are configured to contact at least one electrode, and wherein the configuration of said conductive regions is configured to define an operating electrode unit, on the head of a human subject;

b. contacting the conductive regions of said electrode headset grid with a plurality of electrodes;

c. inducing a non-invasive electrical stimulation of the brain of said human subject via the plurality of electrodes; and d. inducing EEG measurement of electrical currents within a brain of said human subject via the plurality of electrodes, thereby obtaining EEG signals.

In other embodiments, the method includes:

a. placing an electrode headset grid adapted to fit on the head of a human subject, the grid comprising a plurality of conductive regions, electrically isolated from each other, wherein said conductive regions are configured to contact at least one electrode, and wherein the configuration of said conductive regions is configured to define an operating electrode unit, on the head of a human subject;

b. contacting the conductive regions of said electrode headset grid with a plurality of electrodes;

c. inducing EEG measurement of electrical currents within a brain of said human subject via the plurality of electrodes, thereby obtaining EEG signals;

d. inducing a non-invasive electrical stimulation of the brain of said human subject via the plurality of electrodes; and e. inducing EEG measurement of electrical currents within a brain of said human subject via the plurality of electrodes, thereby obtaining EEG signals.

The method of carrying out integrated non-invasive brain electrical stimulation and monitoring may further comprise processing, storing, displaying and/or analyzing EEG signals obtained from the plurality of electrodes.

In the preferred embodiments of the invention, the EEG measurement and the electrical stimulation are performed via the same plurality of electrodes. In further embodiments, each of the plurality of electrodes can be used both for the EEG measurement and for the electrical stimulation.

According to some embodiments, the non-invasive stimulation is performed according to a predefined algorithm. In further embodiments, the method includes a step of defining the EEG monitoring and/or stimulation parameters. In still further embodiments, the algorithm is configured to define said EEG monitoring and/or stimulation parameters. Said EEG monitoring and/or electrical stimulation parameters include, but are not limited to, polarity of the electrodes, including an anode, a cathode or a combination thereof; current type, including DC, AC or a combination thereof; stimulation current amplitude; stimulation current waveform; stimulation current pulse length; or electrode mode of functioning, including working, reference, non-functioning or a combination thereof. In further embodiments, the method includes a step of defining the brain region for the EEG monitoring and/or stimulation. In yet further embodiments, the method includes a step of defining the EEG monitoring and/or stimulation parameters relatively to the defined brain region. In other embodiments, the method includes a step of defining the EEG monitoring and/or stimulation parameters relatively to the conductive regions configuration of the electrode headset grid.

According to additional embodiments, the method includes the step of altering the EEG monitoring and/or electrical stimulation parameters. Said step of altering the EEG monitoring and/or electrical stimulation parameters may be performed in response to the obtained EEG signals.

According to further embodiments, the method includes the step of interchanging the electrode headset grid with an electrode headset grid having a different configuration of conductive regions. Said step of interchanging the electrode headset grid may be performed in response to the obtained EEG signals. Said step of interchanging the electrode headset grid may be performed during carrying out EEG monitoring and/or electrical stimulation. According to further embodiments, said step of interchanging the electrode headset grid allows altering at least one of the EEG monitoring and/or electrical stimulation parameters.

According to additional embodiments, said method includes a step of detaching the plurality of electrodes from the conductive regions of said electrode headset grid. The method may further include the step of disposing the electrode headset grid.

Figure 1A:
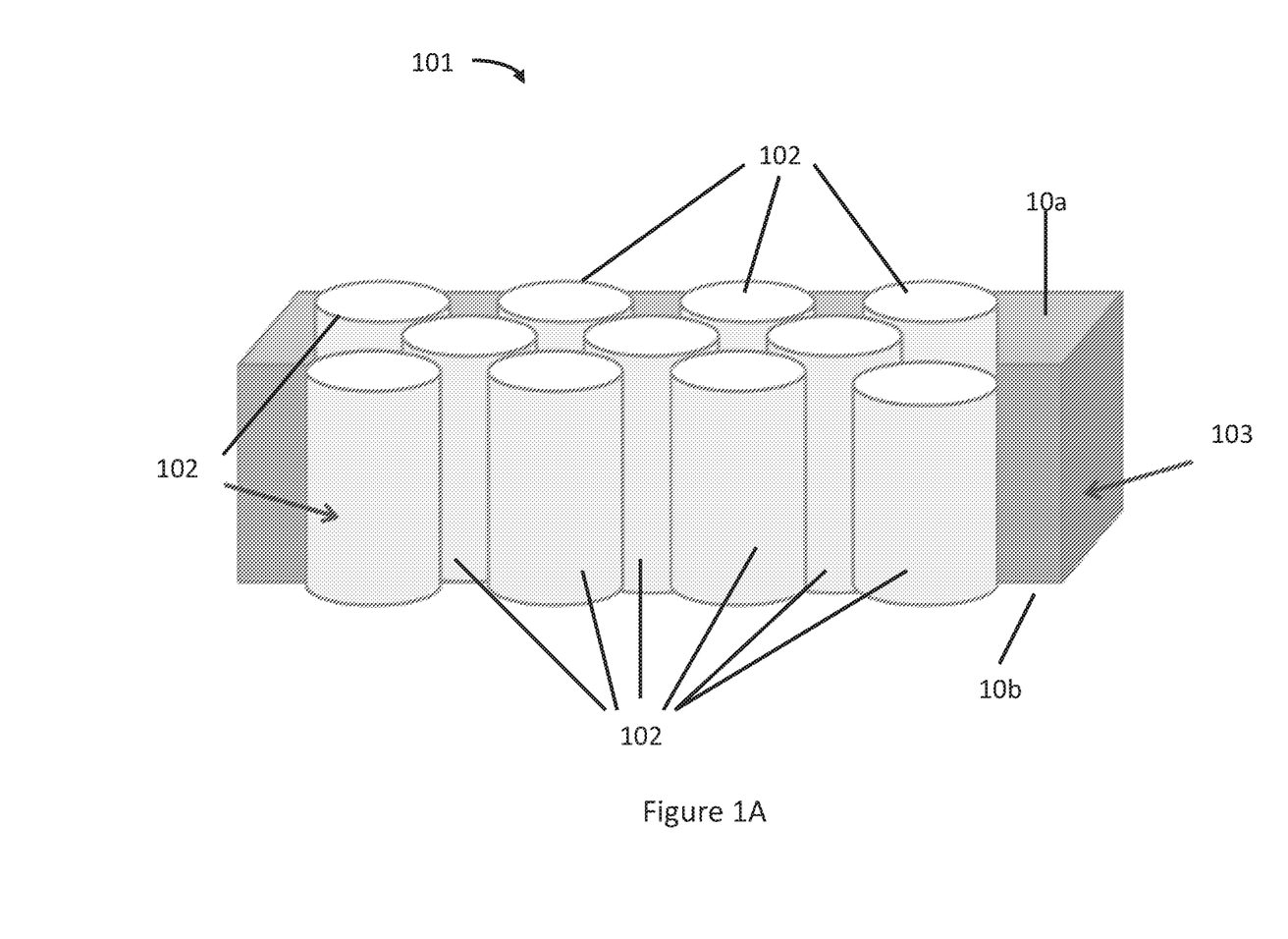
FIG. 1A shows a side view of electrode headset grid 101.

Reference is now made to FIG. 1A which schematically illustrates the side view of electrode headset grid 101, in accordance with an embodiment of the invention.

Figure 4:
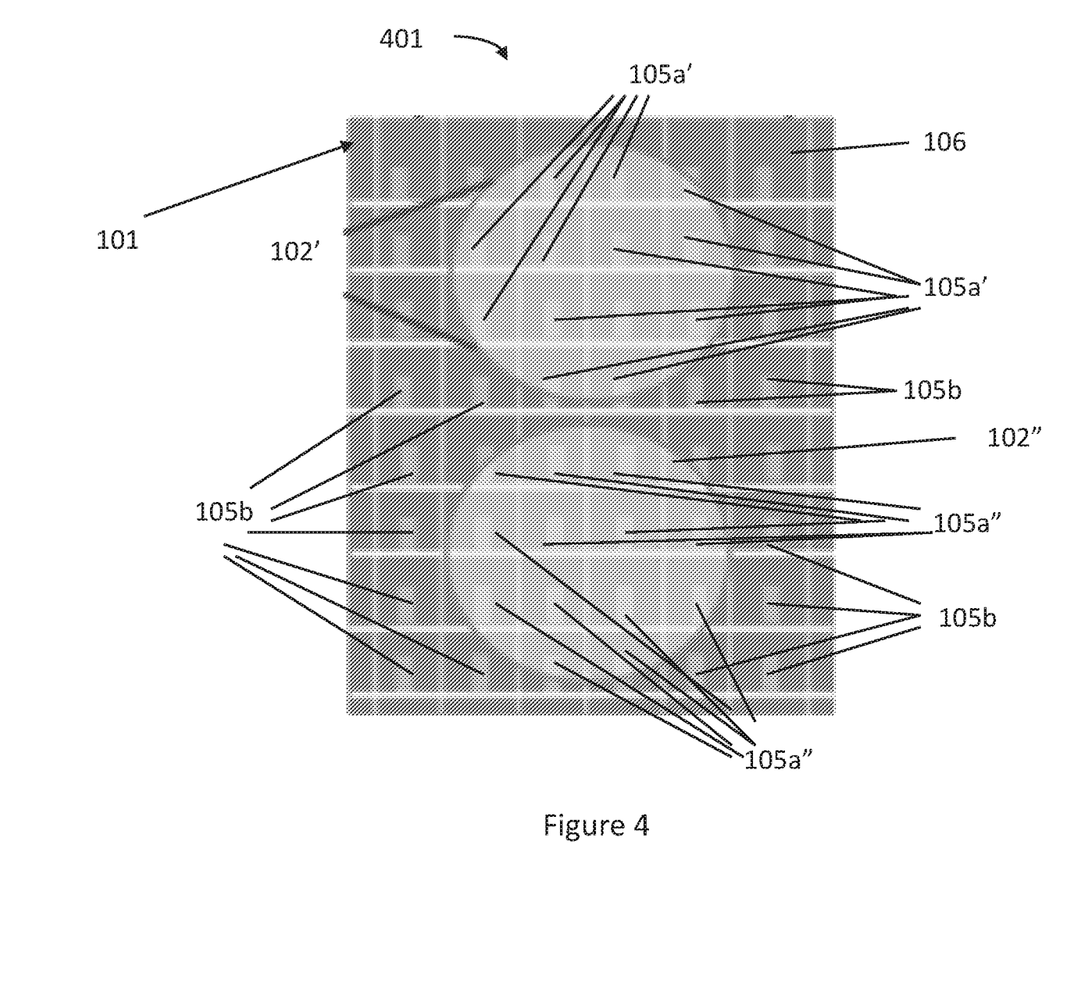
FIG. 4 shows a top view of integrated system 401, including electrode headset grid 101*a* and electrode array 301.

Electrode headset grid 101 comprises isolating matrix 103 and a plurality of channels 102 protruding from side 10a of isolating matrix 10a to side 10b of isolating matrix 103, wherein channels 102 are separated from each other by matrix 103. According to some embodiments, said channels are hollow. According to further embodiments, channels 102 are filled with SAP (not shown). Each of the plurality of channels 102 is configured to contact at least one electrode (as shown in FIG. 4).

Figure 1B:
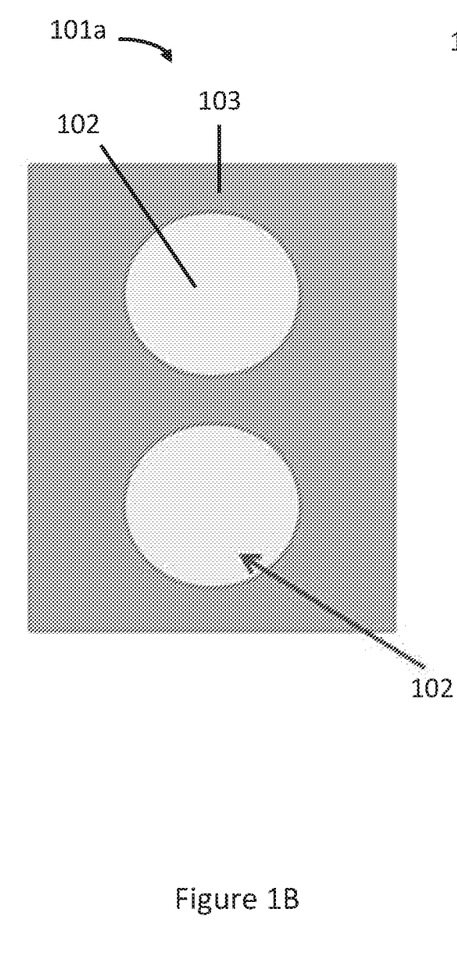
FIG. 1B shows a top view of electrode headset grid 101*a*.
Figure 1C:
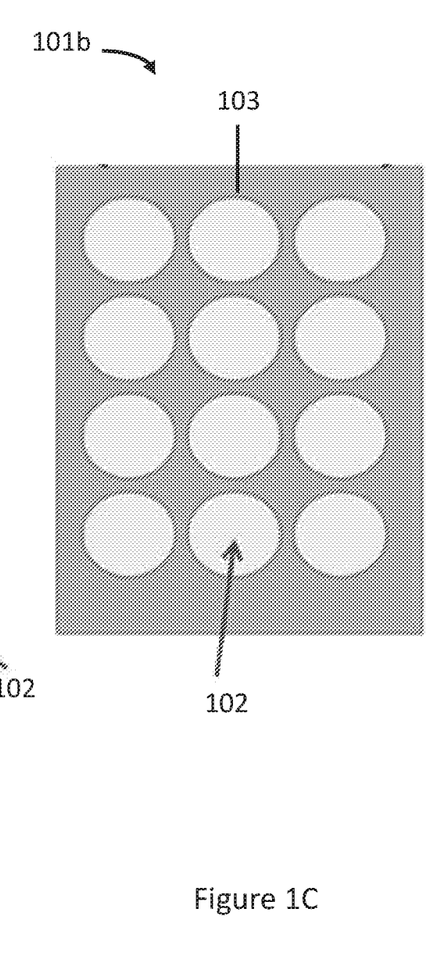
FIG. 1C shows a top view of electrode headset grid 101*b*.
Figure 1D:
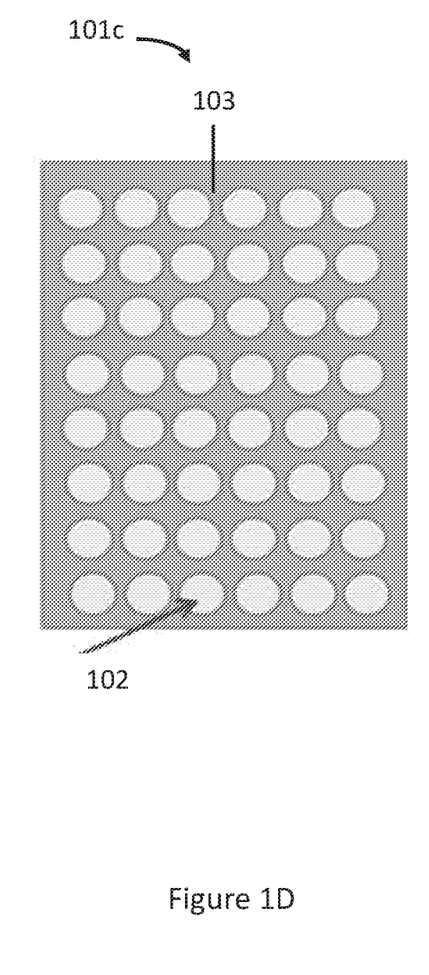
FIG. 1D shows a top view of electrode headset grid 101*c*.

Reference is now made to FIGS. 1B-1D which schematically illustrate the top view of electrode headset grids 101a, 101b and 101c, in accordance with embodiments of the invention.

Each of electrode headset grids 101a, 101b and 101c comprises isolating matrix 103 and a plurality of channels 102. Electrode headset grids 101a, 101b and 101c differ from one another by the number of channels 102. Electrode headset grid 101a includes 2 channels 102, electrode headset grid 101b includes 12 channels 102 and electrode headset 101c includes 48 channels 102. According to some embodiments of the invention, each channel 102 of electrode headset grids 101a, 101b and 101c defines the operating electrode unit. Radius of channels 102 relatively to isolating matrix 103 may be varied according to the required treatment protocol. Electrode headset grid 101a can be interchanged, for example, with electrode headset 101c during the integrated EEG monitoring and stimulation procedure, if a larger number of stimulation sites and/or higher spatial EEG resolution are required. Alternatively, electrode headset grid 101c can be interchanged with electrode headset grid 101a if higher signal-to-noise ratio is desired. Radius of channels 102 in each of electrode headset grids 101a, 101b and 101c can be same or different. The position of channels 102 relatively to isolating matrix 103 and to each other may be varied according to the required treatment protocol. For example, only selected areas of the skull can be stimulated, when electrode headset grid includes channels 102 positioned to coincide with said selected areas of the skull when placed on subject's head.

Figure 2A:
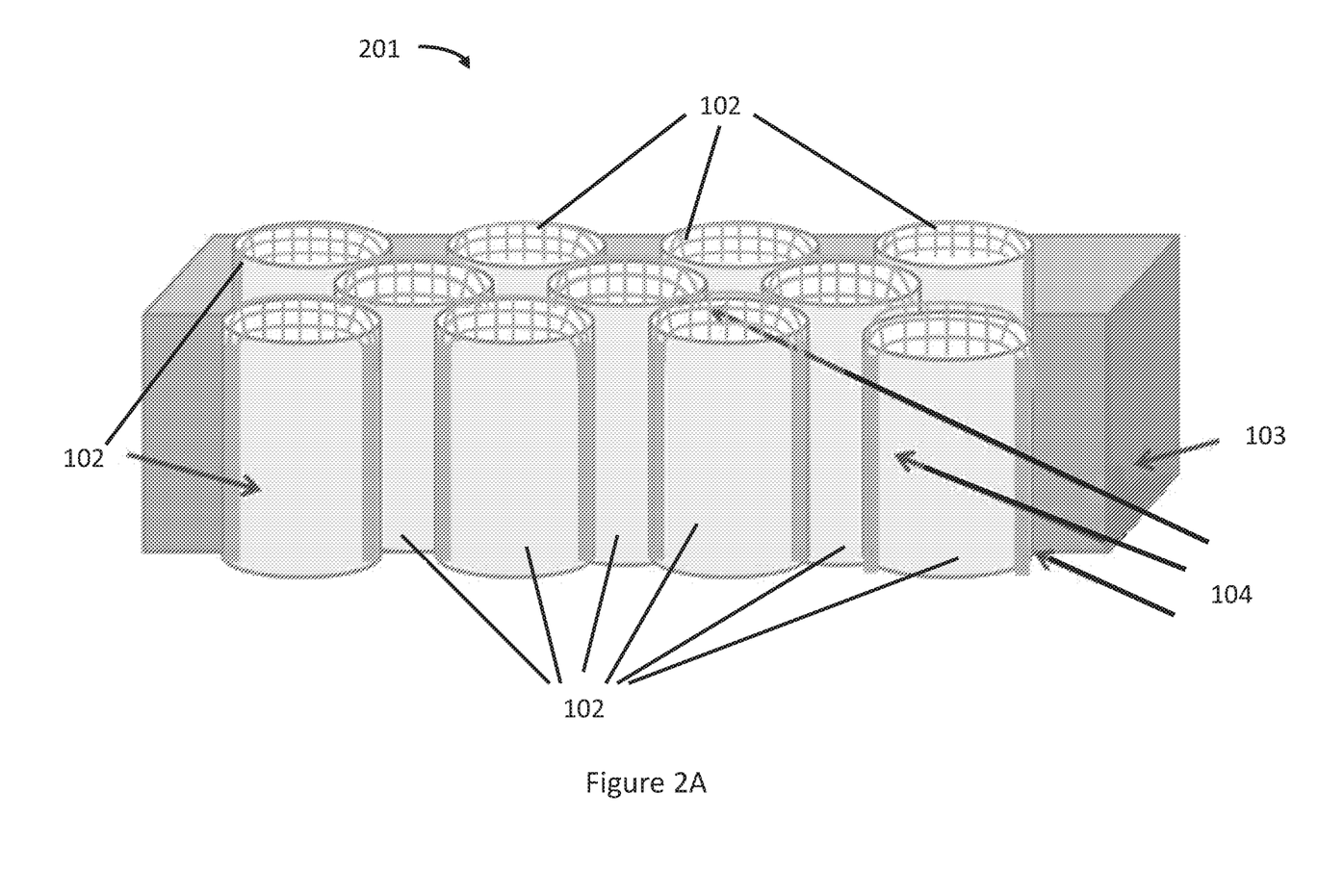
FIG. 2A shows a side view of electrode headset grid 201.

Reference is made to FIG. 2A which schematically illustrates the side view of electrode headset grid 201, in accordance with an embodiment of the invention.

Electrode headset grid 201 comprises isolating matrix 103, a plurality of channels 102 protruding from side 10a of isolating matrix 10a to side 10b of isolating matrix 103, wherein channels 102 are separated from each other by matrix 103 and a plurality of metal inserts 104. According to some embodiments, said channels are hollow. According to further embodiments, channels 102 are filled with SAP (not shown). Each of the plurality of channels 102 is configured to contact at least one electrode 105 (as shown in FIG. 4). Metal inserts 104 are positioned inside hollow channels 102. Metal inserts 104 may be, for example, in a form of a net. Metal inserts 104 are configured to improve electrical contact between electrode 105 (shown in FIG. 4), the SAP and the head of a subject (not shown).

Figure 2B:
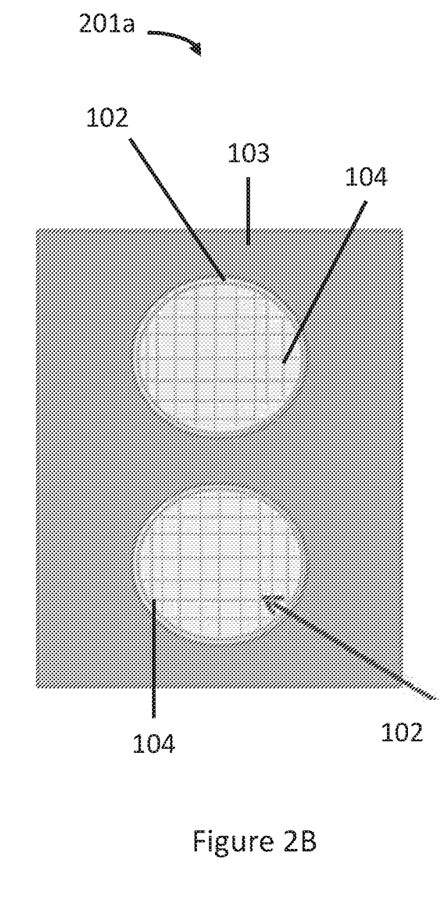
FIG. 2B shows a top view of electrode headset grid 201*a*.
Figure 2C:
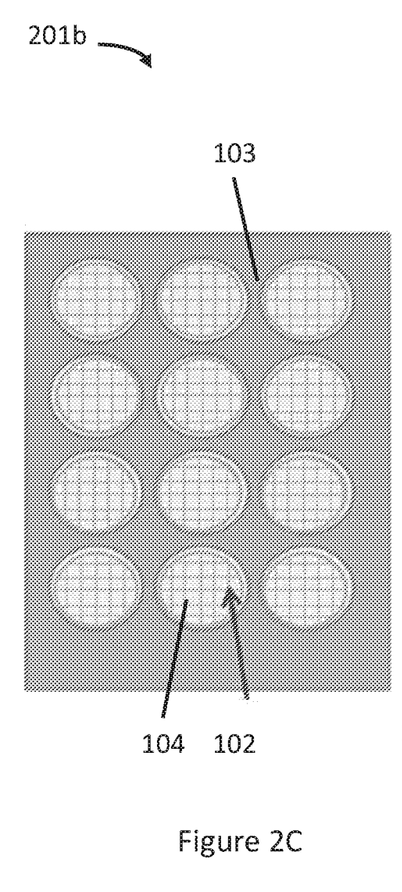
FIG. 2C shows a top view of electrode headset grid 201*b*.
Figure 2D:
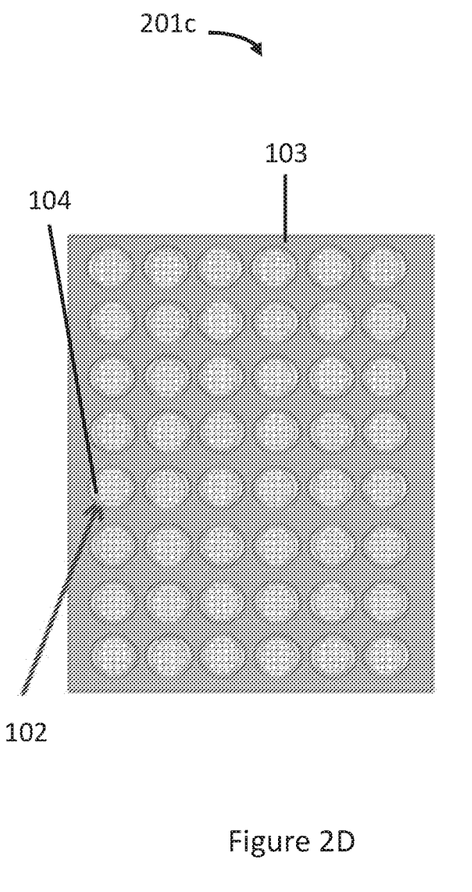
FIG. 2D shows a top view of electrode headset grid 201*c*.

Reference is now made to FIGS. 2B-2D which schematically illustrate the top view of electrode headset grids 201a, 201b and 201c, in accordance with embodiments of the invention.

Each of electrode headset grids 201a, 201b and 201c comprises isolating matrix 103, a plurality of channels 102 and a plurality of metal inserts 104. In some embodiments, metal inserts 104 cover at least one open end of channel 102.

Figure 3A:
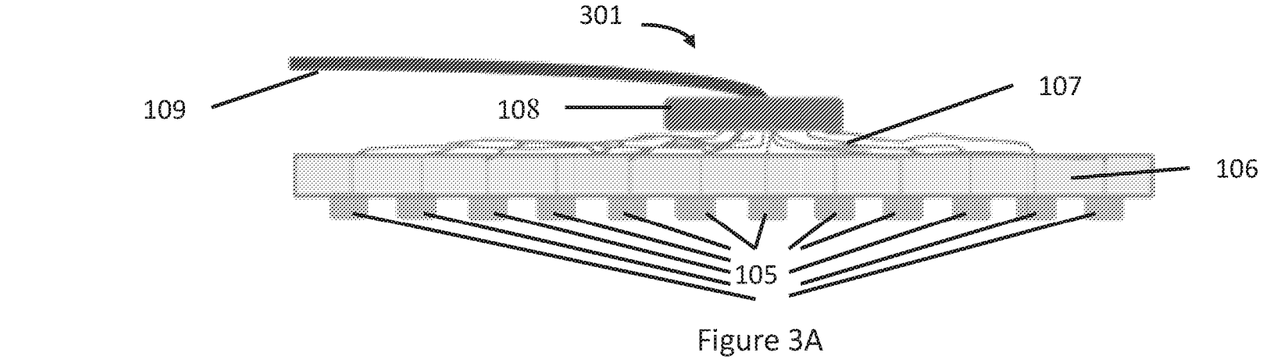
FIG. 3A shows a side view of electrode array 301.

Reference is now made to FIG. 3A which schematically illustrates the side view of electrode array 301, in accordance with an embodiment of the invention.

Electrode array 301 includes a plurality of electrodes 105, connected to isolating board 106 and electrically connected to a plurality of wires 107, wherein each of the plurality of electrodes 105 is connected to at least one wire 106. A plurality of wires 106 is connected to coaxial cable 109 either directly or through pre-amplifier 108.

Figure 3B:
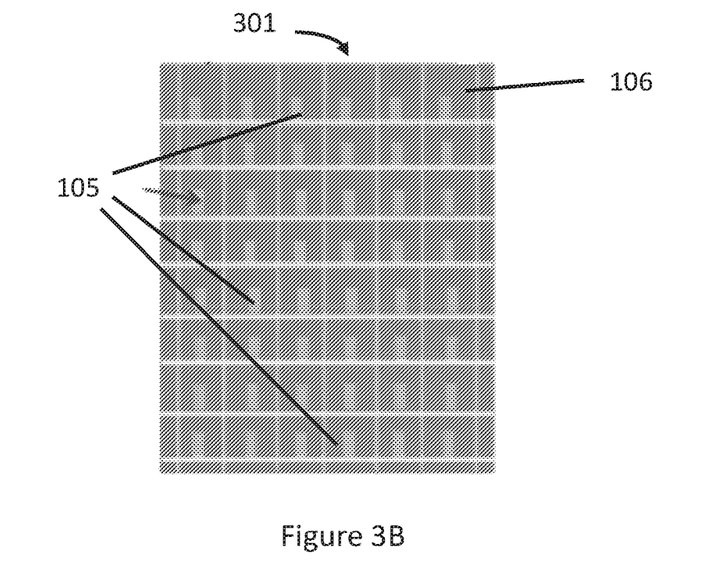
FIG. 3B shows a top view of electrode array 301.

Reference is made to FIG. 3B which schematically illustrates the top view of electrode array 301, in accordance with an embodiment of the invention. Electrode array 301 includes a number of electrodes 105 connected to isolating board 106. In the present example, electrode array 301 includes 48 electrodes.

Reference is now made to FIG. 4 which schematically illustrates the top view of integrated system for brain electric stimulation and EEG monitoring 401, in accordance with an embodiment of the invention.

Integrated system 401 includes electrode array 301 and electrode headset grid 101a. Electrode array 301 contacts electrode headset grid with electrodes 105a, 105a', 105b and 105b' facing electrode headset grid 101a. Electrode headset grid 101a includes isolating matrix 103 and channels 102' and 102" filled with SAP (not shown). Electrodes 105a' coincide with channel 102', such that channel 102' defines an operating electrode unit, wherein all electrodes 105a' are in ionic contact with each other and thus function as one electrode. Electrodes 105a" coincide with channel 102", such that channel 102" defines an operating electrode unit, wherein all electrodes 105a" are in ionic contact with each other and thus function as one electrode. Electrodes 105b do not coincide with channels 102' or 102" of electrode headset grid 101a, such that no electrical connection between them and the head of the subject (not shown) can be established. Thus, in these embodiments electrodes 105b of electrode array 301 are not operating when used with electrode headset grid 101a. In these embodiments, only electrodes 105a' and 105" are operating and can be used as stimulating or EEG electrodes, including anode, cathode, working electrode, reference electrode or a non-functioning electrode, wherein a plurality of electrodes 105a' (contacting channel 102') functions as one separate electrode and a plurality of electrodes 105a" (contacting channel 102") functions as another separate electrode.

If electrode array 301 is used with electrode headset grid 101c (shown in FIG. 1D), which includes 48 channels 102, each of the 48 electrodes 105 of electrode array 301 coincides with channels 102, such that operating electrode unit includes only 1 electrode. In these embodiments, all electrodes 105 are operating and can be used as stimulating or EEG electrodes, including anode, cathode, working electrode, reference electrode or a non-functioning electrode.

While a number of exemplary aspects and embodiments have been discussed above, those of skill in the art will recognize certain modifications, permutations, additions and sub-combinations thereof. It is therefore intended that the following appended claims and claims hereafter introduced be interpreted to include all such modifications, permutations, additions and sub-combinations as are within their true spirit and scope.

In the description and claims of the application, each of the words "comprise" "include" and "have", and forms thereof, are not necessarily limited to members in a list with which the words may be associated.

What is claimed is:

1. An apparatus comprising:
   an electrode array; and
   a plurality of electrode compatible headset grids that are configured to be interchangeably couplable to the electrode array and to be disposed between the electrode array and a head of a subject, each of the electrode compatible headset grids comprising:
      a flexible isolating matrix, configured to isolate electrical current; and
      a plurality of conductive channels, scattered within the isolating matrix, the conductive channels:
         being configured to allow electric communication between one side of the isolating matrix and the other,
         being electrically isolated one from the other by the flexible isolating matrix, and
         being configured to group respective sets of one or more electrodes into operating electrode units via which current passes between the electrode array and the subject's head, wherein a size of each of the conductive channels of each of the electrode compatible headset grids defines for its associated operating electrode unit a number of electrodes that are in ionic contact with each other, and the location of each of the conductive channels within its electrode compatible headset grid defines the location of its associated operating electrode unit, wherein each of the conductive channels of each of the electrode compatible headset grids is configured to group a defined number of electrodes into an operating electrode unit to enable the defined number of electrodes to function as a single electrode, and wherein the plurality of electrode compatible headset grids have different arrangements of conductive channels from each other, such that when coupled to the electrode array, each of the electrode compatible headset grids converts the electrode grid into a different arrangement of operating electrode units.

2. The apparatus according to claim 1, wherein each of the conductive channels of each of the electrode compatible headset grids is hollow.

3. The apparatus according to claim 2, wherein the conductive channels of each of the electrode compatible headset grids is filled with at least one of: a conductive material and metal inserts.

4. The apparatus according to claim 3, wherein said conductive material is at least one of a solid conductive material and a non-leaking conductive material.

5. The apparatus according to claim 3, wherein said conductive material comprises a super absorbent polymer (SAP).

6. The apparatus according to claim 5, wherein said SAP comprises a hydrogel.

7. The apparatus according to claim 6, wherein said SAP comprises a polyacrylate salt.

8. The apparatus according to claim 1, wherein the different arrangement of operating electrode units is configured for a protocol mode, wherein the protocol mode is selected from a predetermined treatment protocol, a predetermined diagnosis protocol and a predetermined treatment and diagnosis protocol.

9. The apparatus according to claim 1, wherein the conductive channels of at least one of the electrode compatible headset grids are non-homogeneously distributed within the isolating matrix.

10. The apparatus according to claim 1, wherein at least one of the conductive channels of at least one of the electrode compatible headset grids is configured to protrude from the isolating matrix.

11. The apparatus according to claim 1, wherein at least one of the conductive channels of at least one of the electrode compatible headset grids has an area of between 0.1 cm2 and 500 cm2.

* * * * *